United States Patent [19]

Immenkeppel et al.

[11] Patent Number: 5,091,562
[45] Date of Patent: Feb. 25, 1992

[54] PROCESS FOR ELIMINATING 1-CARBOXY-1-PHOSPHONOCYCLOPEN-TAN-3-ONE FROM, OR REDUCING ITS CONTENT IN, TECHNICAL 2-PHOSPHONOBUTANE-1,2,4-TRICARBOXYLIC ACID USING BLEACHING LIQUOR

[75] Inventors: Michael Immenkeppel, Bonn; Roland Kleinstück, Bergisch Gladbach; Hans-Dieter Block, Leverkusen; Hermann Sicius, Düsseldorf; Peter Schmidt, Leverkusen, all of Fed. Rep. of Germany

[73] Assignee: Bayer Aktiengesellschaft, Leverkusen, Fed. Rep. of Germany

[21] Appl. No.: 676,051

[22] Filed: Mar. 27, 1991

[30] Foreign Application Priority Data

Apr. 7, 1990 [DE] Fed. Rep. of Germany ....... 4011379

[51] Int. Cl.⁵ ............................................. C07F 9/38
[52] U.S. Cl. ....................................................... 562/24
[58] Field of Search ........................................... 562/24

[56] References Cited

U.S. PATENT DOCUMENTS

| | | | |
|---|---|---|---|
| 3,886,204 | 5/1975 | Geffos et al. | 562/24 |
| 3,886,205 | 5/1975 | Geffos et al. | 562/24 |
| 3,923,876 | 12/1975 | Heins et al. | 562/24 |
| 4,020,101 | 4/1977 | Gettos et al. | 562/24 |
| 4,931,586 | 6/1990 | Kleinshuck et al. | 562/24 |

FOREIGN PATENT DOCUMENTS

| | | | |
|---|---|---|---|
| 0358022 | 3/1990 | European Pat. Off. | |
| 2061838 | 6/1972 | Fed. Rep. of Germany | |
| 1423495 | 2/1976 | United Kingdom | 562/24 |

Primary Examiner—Bruce Gray
Attorney, Agent, or Firm—Sprung, Horn, Kramer & Woods

[57] ABSTRACT

The present invention relates to a process for eliminating 1-phosphono-1-carboxycyclopentan-3-one (ketone) from, or reducing its content in, an aqueous solution of 2-phosphonobutane-1,2,4-tricarboxylic acid, characterized in that the solution is adjusted to a pH value of > 6 using an aqueous inorganic base, particularly sodium hydroxide, and aqueous bleaching liquor is subsequently added in a molar ratio of NaOCl to ketone of >5:1.

5 Claims, No Drawings

PROCESS FOR ELIMINATING 1-CARBOXY-1-PHOSPHONOCYCLOPENTAN-3-ONE FROM, OR REDUCING ITS CONTENT IN, TECHNICAL 2-PHOSPHONOBUTANE-1,2,4-TRICARBOXYLIC ACID USING BLEACHING LIQUOR

BACKGROUND OF THE INVENTION

This invention relates to a process for eliminating 1-carboxy-1-phosphonocyclopentan-3-one (hereinafter referred to as "ketone") from, or reducing its content in, technical 2-phosphonobutane-1,2,4-tricarboxylic acid (hereinafter referred to as "PBTC") dissolved in water using bleaching liquor.

The industrial production of the corrosion and scale inhibitor, PBTC, is carried out in three steps. First, dimethyl phosphite is reacted with maleic anhydride to form phosphonosuccinic acid tetramethyl ester which is then converted into 2-phosphonobutane-1,2,4-tricarboxylic acid pentamethyl ester by reaction with methyl acrylate in the presence of sodium methylate as catalyst (DE-OS 2 061 838). The ester is then saponified to PBTC. In this process for the production of PBTC or rather an aqueous solution of PBTC, 1-phosphono-1-carboxycyclopentan-3-one is formed as secondary product, having an adverse effect in certain industrial applications of PBTC or rather aqueous solutions of PBTC or its Na, K or $NH_4$ salts. For example, where PBTC is used in the production of special cleaning preparations, the aqueous solution darkens in color.

Accordingly, the problem addressed by the present invention was to provide a process which would enable this troublesome ketone to be eliminated from the aqueous solution of PBTC, or its content therein to be reduced, without destruction of the active substance PBTC.

DESCRIPTION OF THE PREFERRED EMBODIMENTS

The present invention relates to a process for eliminating 1-phosphono-1-carboxycyclopentan-3-one (ketone) from, or reducing its content in, an aqueous solution of 2-phosphonobutane-1,2,4-tricarboxylic acid, characterized in that the solution is adjusted to a pH value of >6 using an aqueous inorganic base, particularly sodium hydroxide, and aqueous bleaching liquor is subsequently added in a molar ratio of NaOCl to ketone of >5 : 1.

In a particularly preferred embodiment of the process according to the invention, the solution is heated at from 70° to 100° C. after addition of the aqueous bleaching liquor.

In one particular variant of the process according to the invention, the solution is adjusted to a pH value of 9-10 before addition of the bleaching liquor.

The bleaching liquor is preferably added in a molar ratio of NaOCl to ketone of from 12 : 1 to 30 : 1.

The process can be carried out either continuously or discontinuously.

Volatile substances formed during the reaction are removed from the reaction solution by conventional methods.

After the process according to the invention has been carried out, the concentration may be adjusted to any desired value by concentration through evaporation or by dilution with water or with other aqueous solutions, for example sodium hydroxide.

The process according to the invention is illustrated by the following Examples.

EXAMPLES

Example 1

Removal of 1-phosphono-1-carboxycyclopentan-3-one from an aqueous solution of 2-phosphonobutane-1,2,4-tricarboxylic acid:

108 g of a 48.8 (or 48.4) % by weight technical PBTC solution in water (corresponding to a content of 0.195 mol 2-phosphonobutane-1,2,4-tricarboxylic acid (PBTC), disregarding such impurities as phosphonosuccinic and phosphonopropionic acid) containing 1.2 (or 1.6) % by weight (0.0062 or 0.0083 mol) ketone are adjusted to pH 9 (or to pH 10) with 81.5 g (or with 84 g) of 45% by weight sodium hydroxide solution. 91.7 g NaOCl solution (corresponding to 0.168 mol NaOCl, molar ratio NaOCl : ketone 27 : 1 or 20.2 : 1) are added dropwise to this solution while it is kept at a temperature of 50° C. (or 60°/70° C. or 80° C.). The solutions are then heated for another 15 minutes at 100° C. The results are set out in Table 1.

Example 2

540 g of a 48.5% by weight aqueous solution of 2-phosphonobutane-1,2,4-tricarboxylic acid (corresponding to a content of 0.97 mol PBTC) containing 1.5% by weight (0.039 mol) ketone are first adjusted to pH 7.1 by addition of 230 ml 45% NaOH solution. 427 g NaOCL (0.782 mol) are added to the resulting mixture (molar ratio of NaOCl to ketone 20.1 : 1); pH value of the mixture 8.3. The pH value of the reaction mixture is then adjusted to 7.5 by addition of concentrated HCl.

The mixture is then refluxed for 2 hours. The results are set out in Table 2.

Example 3

The procedure is as in Example 2, except that 171.5 g bleaching liquor (0.31 mol NaOCl; molar ratio of NaOCl to ketone 8.1 : 1) are used. In addition, the pH value is adjusted to pH 8 before refluxing. The results are shown in Table 2.

Example 4

The procedure is as in Example 2, except that 427 g bleaching liquor (0.782 mol NaOCl; molar ratio of NaOCl to ketone 20.1 : 1) are used and the pH value is adjusted to pH 13.1 before refluxing. The results are shown in Table 2.

Example 5

270 g industrial PBTC solution (containing 48.6% by weight PBTC and 1.4% by weight ketone) are adjusted to pH 9 by addition of 211 g 45% sodium hydroxide solution and heated to 80.C. Bleaching liquor is added to the reaction mixture in a quantity of 143.4 g (=0.263 mol NaOCl, molar ratio of NaOCl to ketone 14.5 : 1) or 286.8 g (=0.526 mol NaOCl, molar ratio of NaOCl to ketone 29 : 1), after which the solutions are tempered for 20 minutes at 80° C. The results are shown in Table 3.

Example 6

270 g PBTC solution (containing 48.6% by weight PBTC and 1.4% by weight ketone) are adjusted to pH 9 by addition of 211 g 45% sodium hydroxide solution. Bleaching liquor is added to the solution cooled to 20° C. in quantities of 143.4 g (=0.263 mol NaOCl; molar ratio of NaOCl to ketone 14.5 : 1) and 191.2 g (=0.351 mol NaOCl; molar ratio of NaOCl to ketone 19.3 : 1). After the addition, the mixture is stirred for 15 minutes and then left standing for 24 hours at room temperature. The results are set out in Table 4.

Example 7

270 g PBTC solution (containing 48.6% by weight PBTC and 1.4% by weight ketone) are adjusted to pH 13 with 351.2 g 45% potassium hydroxide solution. After cooling of the mixture to approx. 20° C., bleaching liquor is added in a quantity of 191.2 g (=0.351 mol NaOCl; molar ratio of NaOCl to ketone 19.3 : 1). The mixture is stirred for 15 minutes at 20° C. and then left standing for 24 hours at room temperature. The results are set out in Table 5.

Example 8

0.75 g 70% ketone are added to 270 g PTBC solution (containing 48.6% by weight PBTC and 1.4% by weight ketone), so that the ketone content of the PBTC solution is increased to 1.5% by weight.

The pH value of the solution is adjusted to 9 by addition of 137 ml 45% sodium hydroxide solution. After heating of the solution to 80° C., bleaching liquor is added to the solution kept at a constant temperature of 80° C. over a period of 3 minutes in a quantity of 142.1 g (=0.26 mol NaOCl; molar ratio of NaOCl to ketone 12.6 : 1). The reaction mixture is then heated for 1 hour at 70° C. (or 80° C.) or for 20 minutes at 90° C. (or 100° C.). The results are shown in Table 6.

It is understood that the specification and examples are illustrative but not limitative of the present invention and that other embodiments within the spirit and scope of the invention will suggest themselves to those skilled in the art.

TABLE 1

| Test | Quantity of 45% by weight NaOH [g] | Temperature of the solution [°C.] | pH value | Molar ratio of NaOCl to ketone | Mol % ketone before the reaction | Mol % ketone after the reaction |
| --- | --- | --- | --- | --- | --- | --- |
| 1 | 81.5 | 50 | 9 | 27:1 | 3.0 | 0 |
| 2 | 81.5 | 60 | 9 | 27:1 | 3.0 | 0 |
| 3 | 81.5 | 70 | 9 | 27:1 | 3.0 | 0 |
| 4 | 81.5 | 80 | 9 | 27:1 | 3.0 | 0 |
| 5 | 84.0 | 50 | 10 | 27:1 | 3.0 | 0 |
| 6 | 84.0 | 60 | 10 | 27:1 | 3.0 | 0 |
| 7 | 84.0 | 70 | 10 | 27:1 | 3.0 | 0 |
| 8 | 84.0 | 80 | 10 | 27:1 | 3.0 | 0 |
| 9 | 81.5 | 50 | 9 | 20.2:1 | 4.2 | 0 |
| 10 | 81.5 | 60 | 9 | 20.2:1 | 4.2 | 0 |
| 11 | 81.5 | 70 | 9 | 20.2:1 | 4.2 | 0 |
| 12 | 81.5 | 80 | 9 | 20.2:1 | 4.2 | 0 |
| 13 | 84.0 | 50 | 10 | 20.2:1 | 4.2 | 0 |
| 14 | 84.0 | 60 | 10 | 20.2:1 | 4.2 | 0 |
| 15 | 84.0 | 70 | 10 | 20.2:1 | 4.2 | 0 |
| 16 | 84.0 | 80 | 10 | 20.2:1 | 4.2 | 0 |

TABLE 2

| Test | Quantity of 45% by weight NaOH [g] | pH value | Molar ratio of NaOCl to ketone | Mol % ketone before the reaction | Mol % ketone after the reaction |
| --- | --- | --- | --- | --- | --- |
| 17 | 230 | 7.5 | 20.1:1 | 3.9 | 0.9 |
| 18 | 228 | 8.0 | 8.1:1 | 3.9 | 1.0 |
| 19 | 293 | 13.1 | 20.1:1 | 3.9 | 0 |

TABLE 3

| Test | Molar ratio of NaOCl to ketone | Heating at 80° C. | Mol % ketone before the reaction | Mol % ketone after the reaction |
| --- | --- | --- | --- | --- |
| 20 | 14.5:1 | After 0 min. | 3.7 | 0.1 |
|  |  | After 5 mins. |  | 0 |
|  |  | After 20 mins. |  | 0 |
| 21 | 29:1 | After 0 min. | 3.7 | 0 |
|  |  | After 5 mins. |  | 0 |
|  |  | After 20 mins. |  | 0 |

TABLE 4

| Test | Molar ratio of NaOCl to ketone | Heating at 20° C. | Mol % ketone before the reaction | Mol % ketone after the reaction |
| --- | --- | --- | --- | --- |
| 22 | 14.5:1 | After 0 h | 3.7 | 3.7 |
|  |  | After 4 h |  | 0.4 |
|  |  | After 8.5 h |  | 0.3 |
|  |  | After 24 h |  | 0.2 |
| 23 | 19.3:1 | After 0 h | 3.7 | 3.2 |
|  |  | After 4.5 h |  | 0.4 |
|  |  | After 9 h |  | 0.3 |
|  |  | After 24 h |  | 0.3 |

TABLE 5

| Test | Heating at 20° C. | Mol % ketone before the reaction | Mol % ketone after the reaction |
|---|---|---|---|
| 24 | After 0 h | 3.7 | 1.4 |
|  | After 4.5 h |  | 0.3 |
|  | After 9 h |  | 0.2 |
|  | After 24 h |  | 0.2 |

TABLE 6

| Test | Heating |  | Mol % ketone before the reaction | Mol % ketone after the reaction |
|---|---|---|---|---|
| 25 | At 70° C. | after 0 min. | 3.8 | 0 |
|  |  | after 10 mins. |  | 0 |
|  |  | after 60 mins. |  | 0 |
| 26 | At 80° C. | after 10 mins. | 3.8 | 0 |
|  |  | after 60 mins. |  | 0 |
| 27 | At 90° C. | after 5 mins. | 3.8 | 0 |
|  |  | after 20 mins. |  | 0 |
| 28 | At 100° C. | after 5 mins. | 3.8 | 0 |
|  |  | after 20 mins. |  | 0 |

What is claimed is:

1. A process for eliminating 1-phosphono-1-carboxycyclopentan-3-one (ketone) from, or reducing its content in, an aqueous solution of 2-phosphonobutane-1,2,4-tricarboxylic acid, wherein the solution is adjusted to a pH value of >6 using an aqueous inorganic base, and then a bleaching liquor is added in an amount sufficient to provide a molar ratio of NaOCl to ketone of >5 : 1.

2. A process according to claim 1, wherein the solution is heated at from 70° to 100° C. after addition of the aqueous bleaching liquor.

3. A process according to claim 1, wherein the solution is adjusted to a pH value of from 9 to 10 before addition of the bleaching liquor.

4. A process according to claim 1, wherein the bleaching liquor is added in an amount sufficient to provide a molar ratio of NaOCl to ketone of from 12 : 1 to 30 : 1.

5. A process according to claim 1, wherein the aqueous inorganic base used is sodium hydroxide.

* * * * *